United States Patent [19]

Walton

[11] Patent Number: 4,753,793

[45] Date of Patent: Jun. 28, 1988

[54] HAIR CONDITIONING PREPARATION

[75] Inventor: Ian B. Walton, Cheshire, England

[73] Assignee: Lever Brothers Company, New York, N.Y.

[21] Appl. No.: 644,419

[22] Filed: Aug. 27, 1984

[30] Foreign Application Priority Data

Sep. 16, 1983 [GB] United Kingdom ................ 8324858

[51] Int. Cl.$^4$ .......................... A61K 7/06; A61K 7/09
[52] U.S. Cl. ......................................... 424/70; 424/71
[58] Field of Search .................................... 424/70, 71

[56] References Cited

U.S. PATENT DOCUMENTS

| | | | |
|---|---|---|---|
| 3,144,391 | 8/1964 | Goff | 424/71 |
| 3,910,862 | 10/1975 | Barabas et al. | 525/326.9 |
| 3,959,462 | 5/1976 | Parks et al. | 424/70 |
| 4,247,538 | 1/1981 | Barker | 424/70 |

FOREIGN PATENT DOCUMENTS

| | | | |
|---|---|---|---|
| 757957 | 4/1971 | Belgium | 424/70 |
| 34190 | 8/1981 | European Pat. Off. . | |
| 1467925 | 1/1968 | Fed. Rep. of Germany | 424/70 |
| 56-22717 | 3/1981 | Japan | 424/70 |
| 57-126409 | 4/1982 | Japan . | |
| 1268636 | 3/1972 | United Kingdom . | |
| 1312675 | 4/1973 | United Kingdom . | |
| 1329242 | 9/1973 | United Kingdom . | |
| 2000026 | 1/1979 | United Kingdom . | |
| 1572626 | 7/1980 | United Kingdom . | |
| 2114580 | 8/1983 | United Kingdom . | |

OTHER PUBLICATIONS

Technical Service Report G2a, Vinyl Products Ltd.
Balsam and Sagarin, eds., Cosmetics Science and Technology, (Wiley–Interscience), pp. 365–372.
Harry's Cosmeticology (Leondard Hill Books), pp. 434–436.
Jellinek, Formulation and Function of Cosmetics, (Wiley–Interscience), pp. 258–260.
Harry, Modern Cosmeticology, vol. I (Leonard Hill Books Ltd.), pp. 421–422.

*Primary Examiner*—Albert T. Meyers
*Assistant Examiner*—F. Krosnick
*Attorney, Agent, or Firm*—Milton L. Honig; James J. Farrell

[57] ABSTRACT

There is disclosed a hair rinse conditioner which is capable of imparting a degree of set to the hair. The conditioner comprises, in an aqueous medium, a cationic surfactant which is present in lamellar phase and a latex of particles of a water-insoluble film-forming polymer, which latex has a minimum film-forming temperature in the range 15° C. to 50° C.

10 Claims, No Drawings

HAIR CONDITIONING PREPARATION

This invention relates to hair conditioning preparations and in particular to conditioning hair rinses, which are sometimes simply called hair rinses. These products are intended to be applied to wet hair following shampooing, and after rinsing off they leave the hair in an improved condition. In particular this treatment makes the hair more manageable and improves especially the wet-combability of the hair. Such products usually comprise an aqueous solution of a cationic quaternary ammonium compound, for example cetyltrimethylammonium chloride.

This invention is concerned with rinse conditioners which additionally enhance the set or retention of style of the hair.

European patent application No. 80 100 731.1 (publication No. 0 034 190; Helene Curtis Industries, Inc.) relates to hair conditioning rinse compositions having hair holding properties. These comprise an aqueous composition containing from about 0.02 to about 2 weight percent of a water-soluble anionic polymer and from about 0.1 to about 5 weight percent of a cationic surfactant capable of forming a water-insoluble reaction product with the anionic polymer.

A hair rinse conditioner having hair setting qualities is also described in Japanese Patent Application No. 57126-409 (Kao Soap KK). These compositions comprise 0.1 to 10 weight percent of a quaternary ammonium salt, 0.1 to 5 weight percent of a polymer having a cationic radical of ring structure (e.g. poly(dimethyldiallylammonium chloride)) and 0.1 to 30 weight percent of an oily compound consisting of a hydrocarbon, higher alcohol or a silicone.

A hair rinse conditioner comprising a water-soluble copolymer of vinyl pyrollidone and dimethylaminoethyl methacrylate and a cationic surfactant is described in Example 13 of UK Patent Application No. 78 26346 (Publication No. 2 000 026; GAF Corporation).

The inclusion of a water-soluble polymer as described in the above Japanese and UK patent applications, respectively, has a limited effect since the polymer would be substantially rinsed out with the rinsing of the hair. Such disadvantage is referred to in the above European application.

UK Patent Application No. 2 114 580 (L'Oreal) describes a composition suitable for treating the hair, nails and/or skin, which comprises, in an appropriate medium, at least one cationic polymer of the polyamine, polyaminoamide or poly-(quaternary ammonium) type containing amine or ammonium groups in the polymer chain or joined thereto, and at least one anionic latex which is in the form of a colloidal suspension of particles of polymers containing anionic functional groups, in an aqueous or organic liquid phase. Embodiments of such a composition in the form of a rinse-off conditioner are described in Examples 1 and 2 of the application.

The rinse conditioner preparation of the present invention which is capable of imparting a degree of set to the hair comprises, in an aqueous medium, a cationic surfactant which is present in disperse lamellar phase and a latex of particles of a water-insoluble film-forming polymer, which latex has a minimum film-forming temperature of 15° to 50° C., the composition not containing a cationic polymer, i.e. a polymer having cationic functional groups.

Suitable cationic surfactants include quaternary ammonium chlorides and bromides having at least one long chain (C12–C22) alkyl group or at least one aryl group. Specific surfactants which are suitable include oleyl dimethyl benzyl ammonium chloride, cetyl trimethyl ammonium chloride, cetyl trimethyl ammonium bromide, methyl bis[2-hydroxyethyl] oleyl ammonium chloride, stearyl trimethyl ammonium chloride and distearyl dimethyl ammonium chloride. The cationic surfactant is generally used in amounts from about 0.1 to about 5 weight percent. A preferred range is from about 0.2 to about 3 weight percent by weight.

The cationic surfactant of the hair rinse conditioner of this invention is present in the aqueous composition as a disperse lamellar phase rather than in micellar form as it does in a simple aqueous solution. The production of a disperse lamellar phase is most conveniently effected by the inclusion of higher fatty alcohols having 8–22, preferably 16–20, carbon atoms, such as cetyl and stearyl alcohols, which themselves contribute to the overall conditioning properties of the product. Such higher alcohols may range in amount from 0.1 to 5 weight percent of the total composition, the amount being sufficient to convert the surfactant to the lamellar liquid crystal phase.

The water-insoluble film-forming polymer present in the rinse conditioner composition of the present invention is incorporated as a latex emulsion having a minimum film-forming temperature of from 15° to 50° C., preferably from 15° to 35° C. The polymer emulsion is preferably one which produces films having a measurable hardness as determined by the Persoz method.

Examples of suitable polymer types are poly (vinyl acetate), copolymers of styrene and alkyl acrylates, and copolymers of vinyl acetate and acrylic acid. These polymers are available commercially in the form of latices which usually have a solids content of about 50% by weight. The size of the polymer particles in such a latex usually ranges from about 0.1 micron to about 5 microns.

The amount of the water-insoluble film-forming polymer present in a composition according to the invention is desirably at least 0.5%, preferably at least 1%, by weight of the composition. The amount of the polymer will usually be in the range 1 to 10% by weight of the composition.

Other optional ingredients which may be included in the hair rinse conditioner of the invention include hydrocarbon oils or waxes, silicones, pearlising agents, preservatives, perfumes and colourants.

It is an important feature of this invention that the cationic surfactant is present as a disperse lamellar phase. We have shown that when the cationic surfactant is present only in the micellar form the deposition onto the hair of the particles of the water-insoluble polymer is much reduced resulting in inferior setting properties. In the absence of the cationic surfactant altogether substantially no deposition of polymer occurs and no setting benefit is obtained.

In use the rinse conditioner of the invention is employed in the conventional manner. It is applied to wet hair, usually to freshly shampooed hair, the hair is rinsed and then set in the desired configuration. The hair is then dried. Drying is accelerated by applying heat, such as from a hair drier.

The hair setting properties of the conditioner products of the invention are believed to be due to the deposited polymer particles of the latex forming polymer films which act to hold the hairs in place. Particles deposited from a polymer latex having a relatively low film forming temperature may form films even without the use of, say, a hair drier for drying the hair. However, it has been found that maximum benefits are obtained when heat is applied in the drying stage.

The minimum film forming temperature of the polymer emulsion can be determined by the procedure described in Technical Service Report G2a dated December 1973 of Vinyl Products Limited, Carshalton, Surrey, England. In this test procedure a chromium plated copper bar acts as a standard non-porous test surface; it is adapted for the circulation of coolant at one end and for heating at the other and contains small holes at 2.5 cm intervals in which thermistor probes are placed; these are connected through a multi-way switch to an electrical thermometer. To ensure standard conditions, the bar is enclosed in an insulated box having a lid with a viewing panel. A vent conducts air at 40–50% relative humidity over the upper surface of the bar at a flow rate of 25 liter/minute.

For preliminary determinations a large temperature differential is maintained across the test bar. Emulsion is applied at 0.076 mm wet thickness to the bar, and the lid of the box is closed. The emulsion dries, and at some point along the bar there is a change from a continuous to a discontinuous polymer deposit; the temperature of the bar at that point is measured remotely by the electrical thermometer. The bar is then cleaned and set up to give a temperature gradient of 0.4° C./cm, in a range including the preliminary value. The test is repeated, and gives a value of the minimum film forming temperature accurate to 0.5° C.

The Technical Service Report G2a referred to above also includes a description of the Persoz Pendulum method for determining the hardness of a polymer film. The test procedure is to apply emulsion on flat plate glass to give a dry film 0.05 mm thick. After leaving the dry film for 24 hours at 20° C. and a relative humidity of 65%, the plate is positioned on the stand of the Persoz equipment; the pendulum is placed on the polymer film, and is set swinging with an initial deflection of 12° from the vertical. The time in seconds for the deflection to decrease to 4° from the vertical is recorded; the greater this period, the harder the test material.

The invention will now be illustrated by the following Examples. Percentages are by weight.

EXAMPLE 1

A rinse conditioner was made having the following composition.

| | % |
|---|---|
| Cetyltrimethylammonium chloride (50% active) | 1.4 |
| Paraffin Wax (M. Pt. 48–52° C.) | 1.0 |
| Cetostearyl alcohol[1] | 1.75 |
| Glyceryl monostearate | 0.7 |
| Styrene-acrylic copolymer emulsion (49–51% solids)[2] | 5.0 |
| Water to | 100.0 |

[1] also called cetylstearyl alcohol - a mixture of cetyl alcohol and stearyl alcohol
[2] The copolymer had a styrene:acrylic weight ratio of 1:1 and a particle size of about 0.2 micron. The minimum film forming temperature of the latex was 28° C. The hardness (Persoz) of a dried film of the latex was 106 seconds.

The rinse conditioner was made in the following manner. The paraffin wax, cetostearyl alcohol and glyceryl monostearate were heated at about 70° C. together with 90% of the cationic surfactant. The molten fatty ingredients were then added to the water, also heated to about 70° C., with rapid stirring. The mixture was allowed to cool while maintaining stirring. The latex, to which 10% of the cationic surfactant had been added, was then incorporated.

Curled hair switches treated with the above product, in which the cationic surfactant is present in disperse lamellar phase, were compared for tightness of curl and curl strength with those which had been treated with a micellar solution of cetyltrimethylammonium chloride (0.7%) containing the copolymer latex (2.5% solids).

The comparison between the two hair conditioning products was performed in the following way. Each test product was applied, respectively, to a set of six wet hair switches after which the switches were rinsed with water, towel dried, wound on hair rollers having a diameter of about 3 cms and dried at about 50° C. for 1 hour. The curled switches were then removed from the rollers and placed in a humidity cabinet (50% relative humidity, 20° C.) for 3 hours.

Switches treated with the two test products were then compared in pairs by 6 panellists, each panellist comparing four pairs of switches. The curls were assessed visually for tightness of curl and the panellists also assessed curl strength.

The switches treated with the product of the invention were judged to be significantly superior both in tightness of curl and curl strength to those treated with the conditioner product comprising a micellar solution of the surfactant. The degree statistical significance achieved in these tests was better than 5%.

EXAMPLE 2

A rinse conditioner was made having the following composition.

| | % |
|---|---|
| Cetyltrimethylammonium chloride (50% active) | 1.4 |
| Paraffin Wax (M. Pt. 48–52° C.) | 1.0 |
| Cetostearyl alcohol | 1.75 |
| Glyceryl monostearate | 0.7 |
| Latex of polyvinylacetate[1] (50% solids) | 5.0 |
| Water to | 100.0 |

[1] The copolymer had a particle size of about 1–3 microns and the minimum film-forming temperature of the latex was 19° C. The hardness (Persoz) of a dried film of the latex was 280 seconds.

Treatment of hair switches with the above product by the procedure as described in Example 1 imparted hair holding properties to the hair.

EXAMPLE 3

The following is a further example of a rinse conditioner formulation.

| | % |
|---|---|
| Cetyltrimethylammonium chloride (50% active) | 1.4 |
| Pararfin Wax (M. Pt. 48–52° C.) | 1.0 |
| Cetostearyl alcohol | 1.75 |
| Glyceryl monostearate | 0.7 |
| Latex of Example 1 | 5.0 |
| Preservative | 0.2 |
| Perfume | 0.4 |
| Colourant | 0.0007 |
| Water to | 100.0 |

This product has similar hair setting properties to that of Example 1.

EXAMPLE 4

A rinse conditioner was made having the following composition.

|  | % |
|---|---|
| Distearyldimethylammonium chloride | 0.7 |
| Paraffin wax (M. Pt. 48-52° C.) | 1.0 |
| Cetostearyl alcohol | 1.75 |
| Glyceryl monostearate | 0.7 |
| Latex of Example 1 | 5.0 |
| Water to | 100.0 |

Treatment of hair switches with the above product by the procedure as described in Example 1 imparted hair holding properties to the hair.

EXAMPLE 5

The following is an example of a rinse conditioner of the invention which is applied to the hair in the form of a mousse.

|  | % |
|---|---|
| Conditioner of Example 1 | 90 |
| Propellant $F_{12}$ | 10 |

Treatment of hair switches with this product as described in Example 1 imparted hair holding properties to the hair.

What is claimed is:

1. A hair rinse conditioner preparation comprising, in an aqueous medium, about 0.1% to about 5% by weight of the preparation of a cationic surfactant which is present in disperse lamellar phase; from about 0.1% to about 5% by weight of a higher fatty alcohol having 8-22 carbon atoms; and a latex of particles of a water insoluble film-forming polymer, wherein said polymer is present in an amount of from about 0.5% to about 10% by weight of the preparation, which latex has a minimum film-forming temperature of 15° to 50° C., the preparation not containing a cationic polymer.

2. A hair conditioner preparation as claimed in claim 1 wherein the cationic surfactant is a quaternary ammonium salt.

3. A hair conditioner preparation as claimed in claim 1 wherein the cationic surfactant is present in an amount of from about 0.2% to about 3% by weight of the preparation.

4. A hair conditioner preparation as claimed in claim 1 wherein the water-insoluble film-forming polymer is poly(vinyl acetate), a copolymer of styrene and an alkyl acrylate or a copolymer of vinyl acetate and acrylic acid.

5. A hair conditioner preparation as claimed in claim 1 wherein the amount of the water-insoluble film-forming polymer is from about 1% to about 10% by weight of the preparation.

6. A hair rinse conditioner preparation as claimed in claim 1 comprising, in an aqueous medium, about 0.1% to about 0.5% by weight of a quaternary ammonium cationic surfactant which is present in the aqueous medium in disperse lamellar phase and a latex of particles of a water-insoluble polymer selected from the group consisting of poly(vinyl acetate), copolymers of styrene and an alkyl acrylate and copolymers of vinyl acetate and acrylic acid, said latex having a minimum film forming temperature in the range 15° to 50° C. and said water-insoluble polymer constituting about 0.5% to about 10% by weight of the hair conditioner preparation.

7. A hair conditioner preparation as claimed in claim 1 wherein the film forming temperature of said latex is in the range 15° to 35° C.

8. A hair conditioner preparation as claimed in claim 1, wherein the higher fatty alcohol has from 16-20 carbon atoms.

9. A hair conditioner preparation as claimed in claim 1, wherein the higher fatty alcohol is selected from the group consisting of cetyl alcohol, stearyl alcohol and mixtures thereof.

10. A method of preparing an aqueous hair rinse conditioner preparation as claimed in claim 1 comprising preparing a solution of cationic surfactant, the higher fatty alcohol, and water, wherein said solution contains 90% by weight of the total cationic surfactant present in the rinse conditioner preparation; adding the remaining 10% of the cationic surfactant to the latex of particles of the water-insoluble film-forming polymer; and incorporating the resulting latex into said solution.

* * * * *